United States Patent
Hara et al.

(10) Patent No.: US 8,079,643 B2
(45) Date of Patent: Dec. 20, 2011

(54) VEHICLE SEAT

(75) Inventors: Norie Hara, Kariya (JP); Akihiro Matsuyama, Kariya (JP); Kazuhiro Takami, Karya (JP); Mitsuhito Teramoto, Mishima-gun (JP)

(73) Assignees: Toyota Boshoku Kabushiki Kaisha, Aichi (JP); Sekisui Chemical Co., Ltd., Osaka (JP)

( * ) Notice: Subject to any disclaimer, the term of this patent is extended or adjusted under 35 U.S.C. 154(b) by 78 days.

(21) Appl. No.: 12/376,706

(22) PCT Filed: Aug. 8, 2007

(86) PCT No.: PCT/JP2007/065504
§ 371 (c)(1),
(2), (4) Date: Mar. 24, 2009

(87) PCT Pub. No.: WO2008/018492
PCT Pub. Date: Feb. 14, 2008

(65) Prior Publication Data
US 2009/0224581 A1    Sep. 10, 2009

(30) Foreign Application Priority Data

Aug. 10, 2006 (JP) .................... 2006-218186

(51) Int. Cl.
*A47C 7/24* (2006.01)
(52) U.S. Cl. ................................. 297/452.61
(58) Field of Classification Search ........... 297/452.61
See application file for complete search history.

(56) References Cited

U.S. PATENT DOCUMENTS

| 4,439,472 | A | * | 3/1984  | Bell ................... 428/71 |
| 4,469,738 | A | * | 9/1984  | Himelreich, Jr. ........... 428/198 |
| 4,469,739 | A | * | 9/1984  | Gretzinger et al. ......... 428/198 |
| 4,682,818 | A | * | 7/1987  | Morell .................. 297/452.27 |
| 4,753,480 | A | * | 6/1988  | Morell .................. 297/452.27 |
| 5,334,646 | A | * | 8/1994  | Chen ..................... 524/474 |
| 5,336,708 | A | * | 8/1994  | Chen ..................... 524/474 |
| 5,508,334 | A | * | 4/1996  | Chen ..................... 524/474 |
| 5,633,286 | A | * | 5/1997  | Chen ..................... 524/474 |
| 5,702,153 | A | * | 12/1997 | Pliska ................... 297/256.16 |
| 5,707,107 | A | * | 1/1998  | Melone .................. 297/228.1 |
| 5,833,321 | A | * | 11/1998 | Kim et al. ............... 297/452.42 |
| 5,869,164 | A | * | 2/1999  | Nickerson et al. .......... 428/76 |

(Continued)

FOREIGN PATENT DOCUMENTS

JP    2002161484 A  *  6/2002

(Continued)

OTHER PUBLICATIONS

English language Abstract of JP 2004-346172 A (Dec. 9, 2004).

(Continued)

*Primary Examiner* — Rodney B White
(74) *Attorney, Agent, or Firm* — Greenblum & Bernstein, P.L.C.

(57) ABSTRACT

One aspect of the present invention can include a surface layer made of a fabric material and the surface layer covering one or more portions of a top plate main portion, top plate side portions, outside portions, a seat back portion, and a headrest portion has been subjected to an antiallergenic treatment and the antiallergenic treatment is a treatment in which a back side surface of the surface layer is dipped in an antiallergenic agent containing an aromatic hydroxy compound as an active ingredient.

5 Claims, 5 Drawing Sheets

U.S. PATENT DOCUMENTS

| | | | |
|---|---|---|---|
| 6,071,835 A * | 6/2000 | Tang et al. | 442/216 |
| 6,543,844 B1 * | 4/2003 | Ryan et al. | 297/219.12 |
| 6,866,337 B1 * | 3/2005 | Lash | 297/219.1 |
| 7,000,984 B1 * | 2/2006 | Ward | 297/228.12 |
| 7,396,393 B2 | 7/2008 | Inagaki et al. | |
| 2006/0175877 A1 * | 8/2006 | Alionte et al. | 297/180.14 |
| 2006/0232112 A1 * | 10/2006 | Karr | 297/219.12 |
| 2007/0131116 A1 | 6/2007 | Inagaki et al. | |
| 2007/0190287 A1 | 8/2007 | Seto et al. | |
| 2008/0001451 A1 * | 1/2008 | Olson | 297/219.12 |
| 2008/0250934 A1 | 10/2008 | Inagaki et al. | |
| 2009/0127915 A1 * | 5/2009 | Nozawa et al. | 297/452.48 |
| 2009/0140562 A1 * | 6/2009 | Boulware, Sr. | 297/219.1 |

FOREIGN PATENT DOCUMENTS

| | | | |
|---|---|---|---|
| JP | 2003-081727 A | | 3/2003 |
| JP | 2004-290922 A | | 10/2004 |
| JP | 2004-346172 A | | 12/2004 |
| JP | 2005-089947 A | | 4/2005 |
| JP | 2005089947 A | * | 4/2005 |
| WO | 2005/087059 | | 9/2005 |

OTHER PUBLICATIONS

English language Abstract of JP 2004-290922 A (Oct. 21, 2004).
English language Abstract of JP 2003-081727 A (Mar. 19, 2003).
English language Abstract of JP 2005-089947 A (Apr. 7, 2005).
English language Abstract of WIPO 2005/087059 (Sep. 22, 2005).

* cited by examiner

(General formula 7)

FIG. 4

(General formula 8)   (General formula 9)

(General formula 10)

FIG. 5

VEHICLE SEAT

TECHNICAL FIELD

The present invention relates to a vehicle seat capable of reducing allergens such as mites and pollens.

BACKGROUND ART

In recent years, many allergic diseases such as atopic dermatitis, bronchial asthma, and allergic rhinitis have become problematic. A major cause thereof is an increase in allergens in a life space. Examples of the allergens include allergens of mites in the house, particularly house dust mite allergens (Der 1, Der 2) which are abundantly present in the house dust, and Japanese cedar pollen allergens (Cry j 1, Cry j 2) which are rampant in the air mainly in the spring.

In particular, as for the house dust mite allergens, even if the causal house dust mites are eliminated, the dead mites supply a substance with a higher allergenicity to the life space. Therefore, the allergic diseases caused by the allergens are not fundamentally solved. In addition, Cry j 1 and Cry j 2, which are Japanese cedar pollen allergens, are glycoproteins having molecular weights of about 40 kDa and about 37 kDa, respectively. When either of these glycoproteins is adhered to the nasal mucous membrane or the like, it is recognized as a foreign body and causes an inflammatory response.

In order to reduce or inactivate allergens, various techniques have heretofore been proposed. For example, a liquid allergen reducing agent is proposed in JP-A-2003-81727. This allergen reducing agent can effectively reduce the amount of allergens without tainting or destroying a surface of a livingware to which allergens are adhered. In addition, a liquid allergen reducing fiber product is proposed in JP-A-2005-89947. This allergen reducing agent can exhibit an allergen reducing effect while maintaining the original texture of a fiber product. These allergen reducing agents contain an aromatic hydroxy compound as an active ingredient and reduce or inactivate allergens accumulated on the surface or in the interior of a fiber product.

In addition, allergen pollution not only is caused in the house but also spreads in the interior of a vehicle, particularly a car.

For example, a car seat is reclined to a horizontal position, and a child jumps on the car seat. At this time, a large amount of allergens are stirred up in the vehicle interior and a passenger in the car inhales the allergens, and thus, an allergic disease may be caused.

Therefore, in order to reduce symptoms of an allergic disease or to prevent new occurrence of an allergic disease, it is important to eliminate allergens from the space of living environment such as a house and the interior of a car as much as possible or to inactivate allergens by modifying them.

Therefore, there is a need in the art to provide a vehicle seat capable of more effectively reducing or inactivating allergens in the interior of a car.

SUMMARY OF THE PRESENT INVENTION

The present invention can include a vehicle seat, and the like, having a surface layer made of a fabric material and the surface layer covering one or more portions of a top plate main portion, top plate side portions, outside portions, a seat back portion, and a headrest portion has been subjected to an antiallergenic treatment, and the antiallergenic treatment is a treatment in which a back side surface of the surface layer is dipped in an antiallergenic agent containing an aromatic hydroxy compound as an active ingredient According to the invention, a vehicle seat capable of more effectively reducing or inactivating allergens in the interior of a car can be provided.

BRIEF DESCRIPTION OF THE DRAWINGS

FIG. 5 shows the chemical structure for Chemical 3.
10: Vehicle seat
12: Top plate main portion
14: Top plate side portions
16: Outside portions
18: Seat back portion
20: Headrest portion

DETAILED DESCRIPTION OF THE PRESENT INVENTION

That is, a vehicle seat is generally covered with a surface layer made of leather, a fabric material, or the like. The present inventors presumed that when the surface layer is made of a fabric material, a large amount of allergens of such as house dust mites are accumulated on the texture of the surface layer or in the gaps between stitches of the surface layer.

Accordingly, the present inventors examined the state of allergen pollution in the vehicle interior. As a result, they found that the state of allergen pollution becomes worse as the year in which the car was registered is older. In addition, they found that allergens present in the interior of a car are mainly accumulated on the surface layer of the vehicle seat. Further, they found that when the surface layer is made of leather, allergen pollution is not so serious and when the surface layer is made of a fabric material, allergen pollution becomes worse.

Particularly the following two findings are important.

(1) The allergens accumulated on the vehicle seat do not naturally occur in the vehicle interior, but most of them are brought in from the outside of the vehicle. The allergens in the vehicle interior are not derived from those which grow on the surface layer of the vehicle seat to adult insects or become dead bodies. Most of the allergens are adhered to the clothes or the like of a passenger from a sofa or the like in the house and brought in the vehicle interior from the outside of the vehicle via the passenger.

(2) The allergens accumulated on the surface layer of the vehicle seat are not uniformly accumulated on all the portions of the vehicle seat The allergens are mainly accumulated in a top plate main portion, top plate side portions, outside portions, a seat back portion and a headrest portion. Further, the allergens are particularly accumulated in the top plate main portion, top plate side portions, and the seat back portion.

The present invention has been made based on their own investigations and findings as described above.

Hereinafter, the vehicle seat according to the invention will be described in detail.

Figure 1:
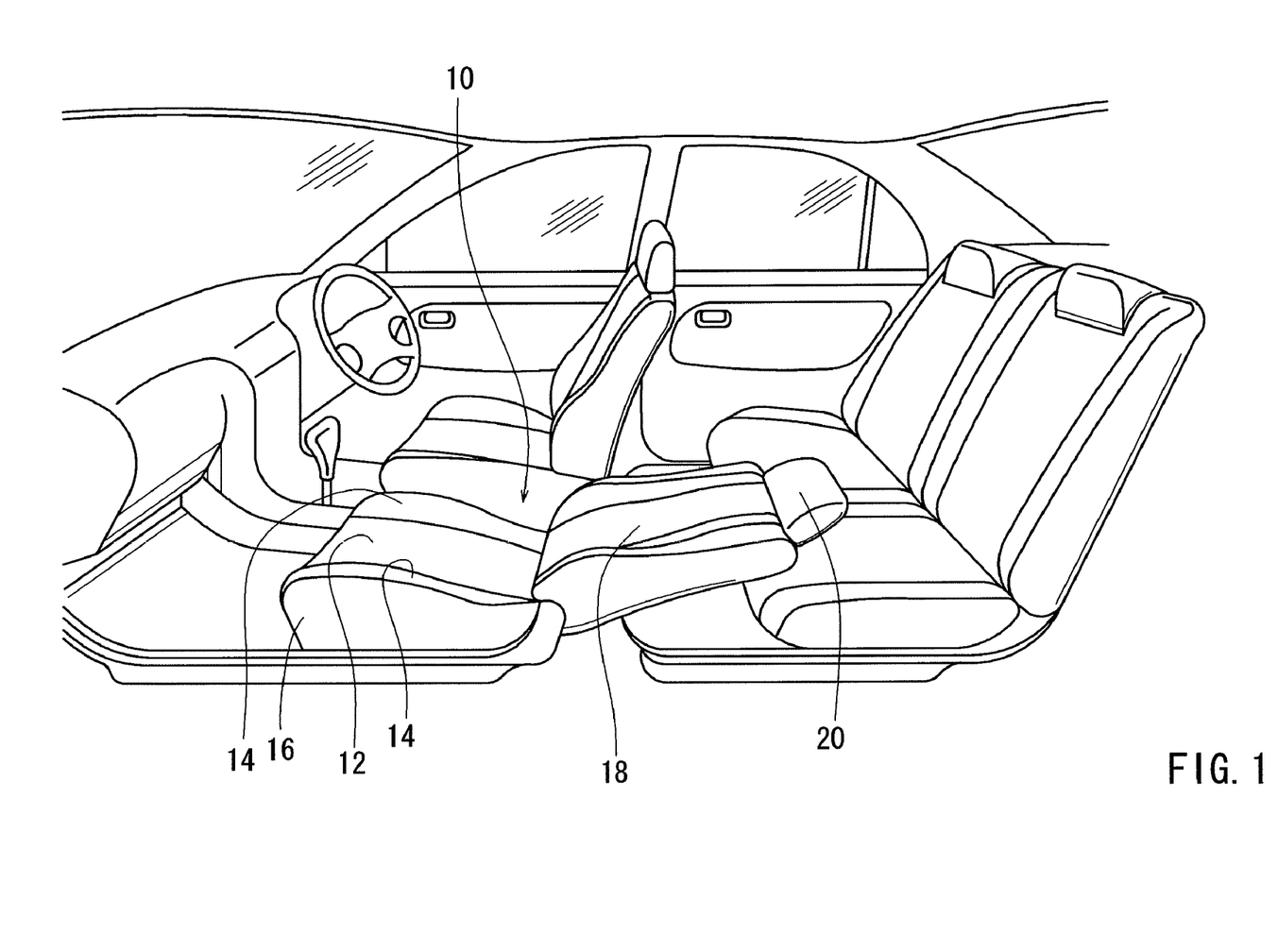
FIG. 1 is a perspective view of a vehicle seat installed in the interior of a car.

A vehicle seat 10 has a top plate main portion 12, top plate side portions 14, outside portions 16, a seat back portion 18, and a headrest portion 20 (FIG. 1). The respective portions of the vehicle seat 10 are covered with a surface layer made of a fabric material. The surface layer covering the respective portions of the vehicle seat 10 has been subjected to an antiallergenic treatment The antiallergenic treatment is a treatment in which a back side surface of the surface layer is dipped in an antiallergenic agent containing an aromatic hydroxy compound as an active ingredient.

In this specification, "back side surface" of the surface layer refers to a surface at the side opposite to the side which comes into contact with a passenger seated on the vehicle seat On the contrary, "front side surface" of the surface layer refers to a surface at the side which comes into contact with a passenger seated on the vehicle seat Specifically, the antiallergenic treatment is a treatment of dipping in an antiallergenic agent containing an aromatic hydroxy compound as an active ingredient. The "treatment of dipping" as used herein refers to a treatment in which a back side surface of the surface layer made of a fabric material is dipped in an antiallergenic agent solution. In other words, in the antiallergenic treatment, the antiallergenic agent penetrates the back side surface of the surface layer. As the method of dipping the surface layer in the antiallergenic agent solution, a technique such as spray printing, gravure printing, or screen printing can be adopted.

When the vehicle seat is polluted with allergens, there is a tendency that the allergens are accumulated not on the front side surface of the surface layer, but in the inside or on the back side surface of the surface layer. Therefore, by dipping the back side surface of the surface layer in the antiallergenic agent solution, the allergens accumulated on the surface layer can be more efficiently inactivated.

Further, in the vehicle seat according to the invention, natural texture or soft touch feeling of the surface layer is maintained. This is because that even if a resin component or the like contained in the antiallergenic agent is solidified, the solidified resin component is prevented from being exposed to the front side surface. Further, in order to maintain the natural texture or soft touch feeling of the surface layer, it is preferred that after the antiallergenic agent is dried, the surface layer is softened by a wringing process or the like.

Figure 3:
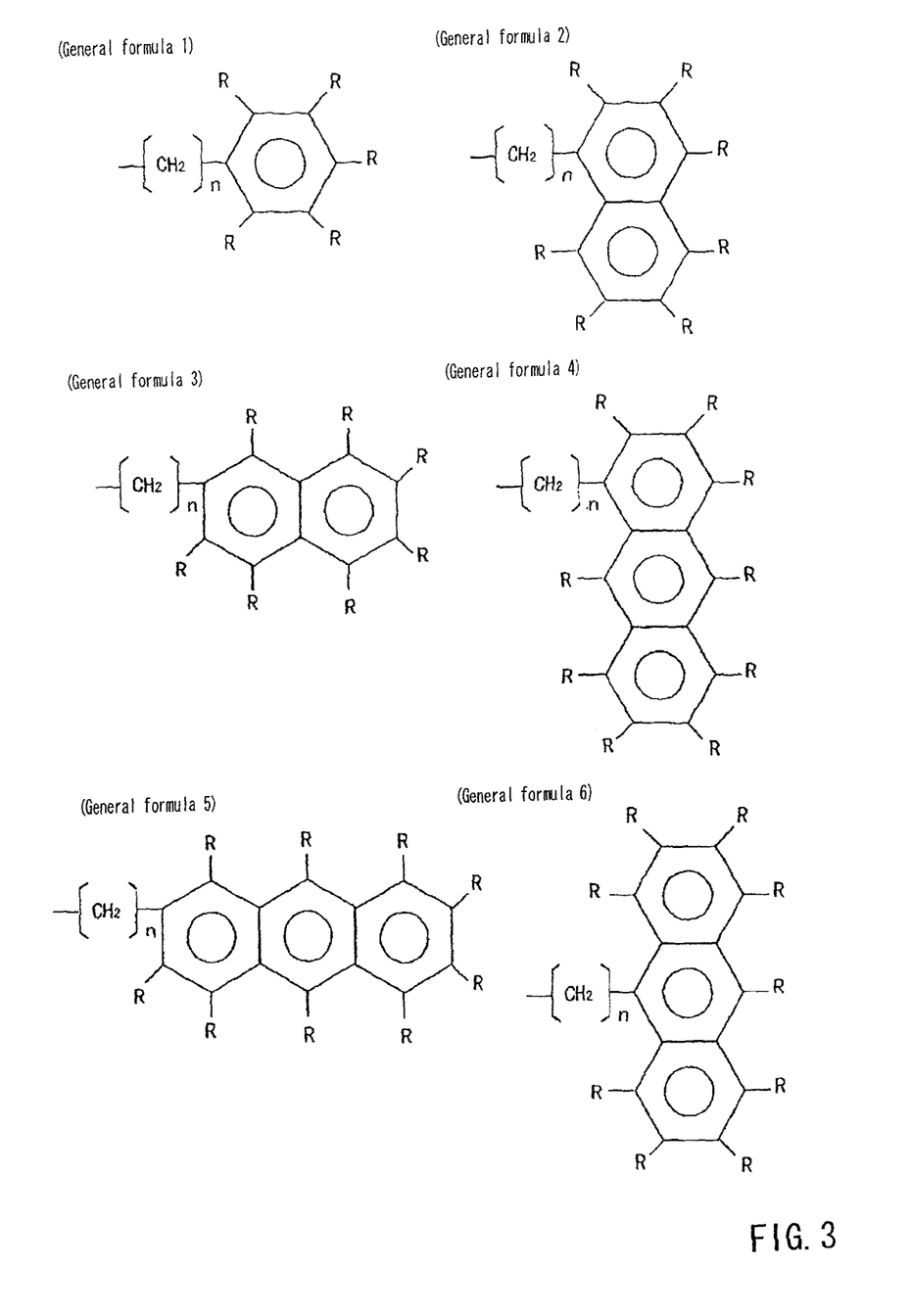
FIG. 3 shows the chemical structure for Chemical 1.

The antiallergenic agent is obtained by adding an allergen reducing substance (an active ingredient) and optionally another additive to a solvent or a binder. The allergen reducing substance to be used as an active ingredient is not particularly limited as long as it is a component capable of inactivating allergens by modifying them or the like and suppressing an antigen-antibody reaction. For example, the allergen reducing substance is preferably, for example, an aromatic hydroxy compound such as tannic acid. This is because the aromatic hydroxyl compound has a high allergen reducing effect. In particular, it is preferably a compound having at least one of functional groups represented by the following general formulae (1) to (6) in a side chain of a linear polymer. This is because this compound has a low risk of ruining a fiber product by coloring.

Please refer to FIG. 3 for Chemical 1

In the general formulae (1) to (6), R represents hydrogen or a hydroxy group, and at least one R represents a hydroxy group; and n represents 0 to 5.

Further, in a compound having a functional group represented by any of the general formulae (1) to (6) in a side chain of a linear polymer, n is from 0 to 5. When n exceeds 5, an effect of using the linear polymer may be lost. In addition, at least one R is a hydroxy group. When the compound does not have a hydroxy group, an allergen reducing effect cannot be sufficiently exhibited in some cases. When the compound has too many hydroxy groups, a coloring property may be exhibited strongly, therefore, the compound preferably has one hydroxy group. Further, as for the position of the hydroxy group, the hydroxy group is preferably bonded to a site with the least steric hindrance. For example, the hydroxy group is preferably in the para position in the case of the general formula (1).

The linear polymer refers to, for example, a vinyl polymer, a polyester, a polyamide, or the like as a synthetic polymer.

Further, the chemical bond between the functional group represented by any of general formulae (1) to (6) and the linear polymer is not particularly limited, and a carbon-carbon bond, an ester bond, an ether bond, an amide bond and the like can be exemplified.

As the compound having a functional group represented by any of the above-mentioned general formulae (1) to (6) in a side chain of a linear polymer, for example, poly(vinyl 3,4,5-hydroxybenzoate), polyvinylphenol, polytyrosine, poly(1-vinyl-5-hydroxynaphthalene), poly(1-vinyl-6-hydroxynaphthalene), or poly(1-vinyl-5-hydroxyanthracene) is preferred. This is because these compounds are safe and easily obtained.

In addition, the aromatic hydroxy compound can be obtained by polymerization or copolymerization of a monomer containing at least one of functional groups represented by the general formulae (1) to (6) and/or a monomer having a monohydric phenol group.

Figure 4:
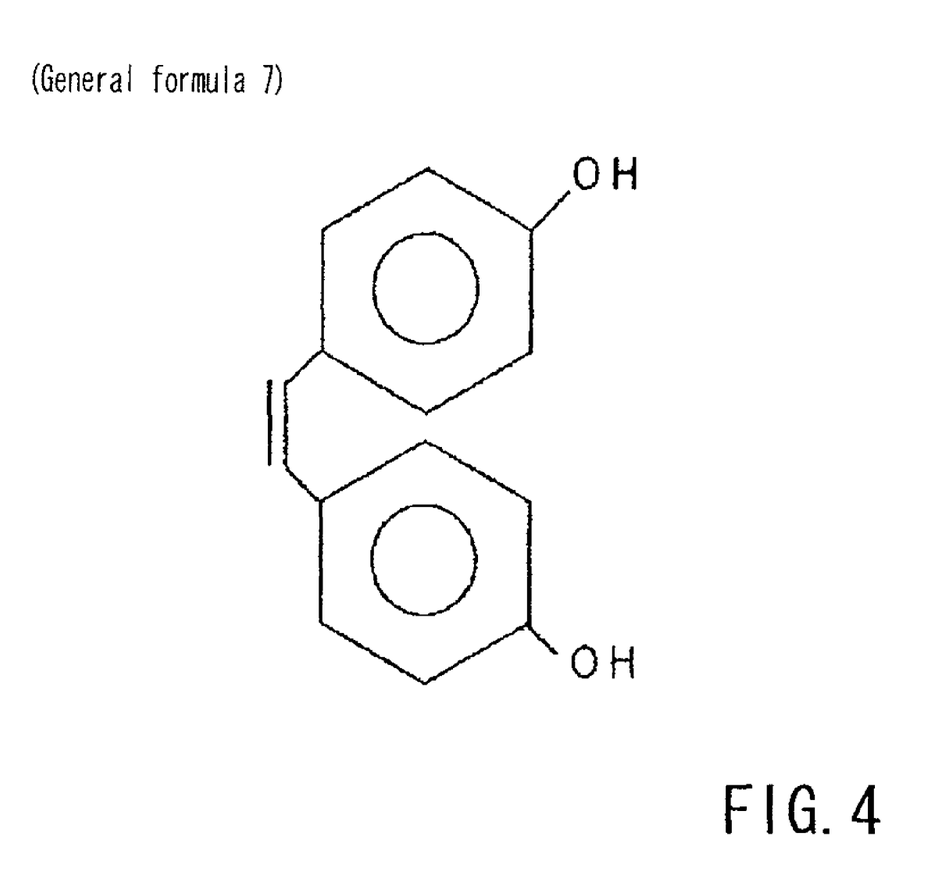
FIG. 4 shows the chemical structure for Chemical 2.

The monomer having one or more monohydric phenol groups is not particularly limited as long as it is a compound in which one or more monomers having one hydroxy group is/are bonded to a benzene ring. Examples of such a compound include vinylphenol, tyrosine and 1,2-di(4-hydroxyphenyl)ethene represented by the following general formula 7. When the active ingredient has a monohydric phenol group, discoloration is difficult to occur as compared with a polyhydric phenol.

Please refer to FIG. 4 for Chemical 2

Another monomer can be copolymerized with the monomer having one or more monohydric phenol groups. As another monomer, ethylene, acrylate, methacrylate, methyl methacrylate, hydroxyethyl methacrylate, hydroxyethyl acrylate, hydroxypropyl acrylate, hydroxypropyl methacrylate, styrene and the like can be exemplified.

The compound obtained by polymerization or copolymerization of the monomer is not particularly limited. For example, a compound obtained by polymerization of at least two or more of the monomers having a monohydric phenol group is preferred, In addition, a compound obtained by polymerization of 5 or more of the above-mentioned monomers having a monohydric phenol group is more preferred.

The aromatic hydroxy compound is preferably an aromatic heterocyclic hydroxy compound.

The aromatic heterocyclic hydroxy compound is not particularly limited. Examples thereof include 2-hydroxyfuran, 2-hydroxythiophene, hydroxybenzofuran and 3-hydroxypyridine. Further, it can be a compound containing an aromatic heterocyclic hydroxy group in a side chain of a linear polymer, a compound obtained by polymerization or copolymerization of a monomer having an aromatic heterocyclic hydroxy group or the like.

Figure 5:
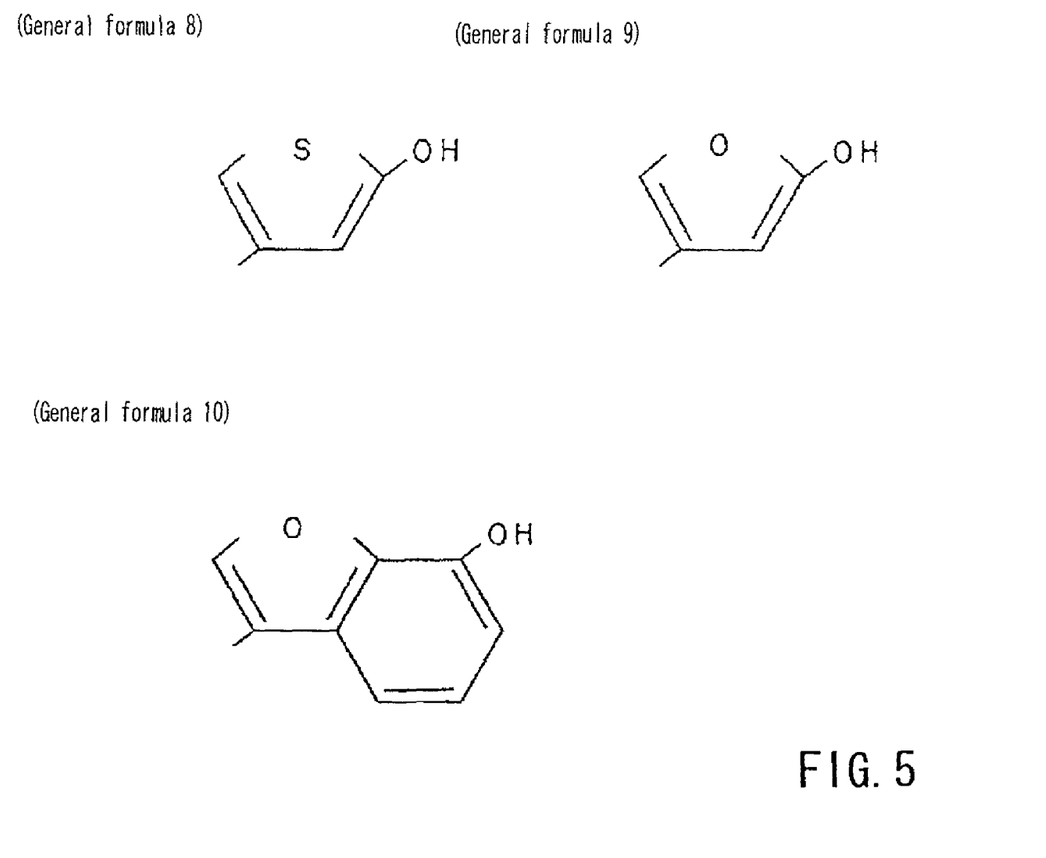

Examples of the aromatic heterocyclic hydroxy group include a group in which a hydroxy group is bonded to a heterocyclic skeleton such as thiophene or furan represented by the following general formula 8 or 9 and a group in which a hydroxy group is bonded to a skeleton having a heterocyclic ring and an aromatic ring represented by the following general formula 10. Examples of it also include a group having a hydroxy group and an alkyl group (having 5 or less carbon atoms) in a heterocyclic skeleton and a group having a hydroxy group and an alkyl group (having 5 or less carbon atoms) in a skeleton with a heterocyclic ring and an aromatic ring.

Please refer to FIG. 5 for Chemical 3

In the vehicle seat according to the invention, an amount of the antiallergenic agent adhered to the surface layer is preferably 2.0 g/m² or more. The reason is as follows.

The present inventors examined the state of allergen pollution on a vehicle seat using a commercially available allergen assay kit (trade name "DaniScan" manufactured by Asahi Food & Health Care Co., Ltd.). As a result, it was found that on a surface layer of a vehicle seat of a car which was used for 50 days in a usual manner, the evaluation value reached "4" which is a high pollution level. The pollution level of "4" corresponds to 8 µg/g of dust in terms of an accumulated amount of mite allergens. That is, it means that when a car is used for 50 days, 8 µg of mite allergens per gram of dust are accumulated. When this value is converted into an accumulated amount per day, 0.16 µg (8 µg/50 days=0.16 µg/day) of mite allergens per gram of dust are accumulated.

According to literature, the amount of dust per unit area of carpet is generally about 0.25 g/m². In the case of a surface layer of a vehicle seat, the amount of dust is presumed to be equal to that in the case of carpet. Accordingly, an accumulated amount of mite allergens per day on a surface layer of a vehicle seat is presumed to be about 0.04 µg/m² (0.25×0.16=0.04 µg/m²).

In the case where a new car is purchased, the first MOT test should be done when the car is three years old, and the next MOT test should be done two years later. Therefore, it is preferred that an allergen reducing effect of the antiallergenic treatment lasts at least 3 years or more, preferably 5 years or more. In consideration of an accumulated amount of mite allergens of 0.04 µg/m² in the case where a car is used for one day, an accumulated amount of mite allergens in the case where a car is used for 3 years is presumed to be 0.04 (µg)× 365 (days)×3 (years)≈44 µg/m², and an accumulated amount of mite allergens in the case where a car is used for 5 years is presumed to be 0.04 (µg)×365 (days)×5 (years)=73 µg/m².

It should be noted here that the presumption and calculation of the accumulated amount of allergens on a vehicle seat as described above are based on our own finding that allergens accumulated on a vehicle seat is attributed to dust mites and the like brought in mainly from the outside of the vehicle.

Figure 2:
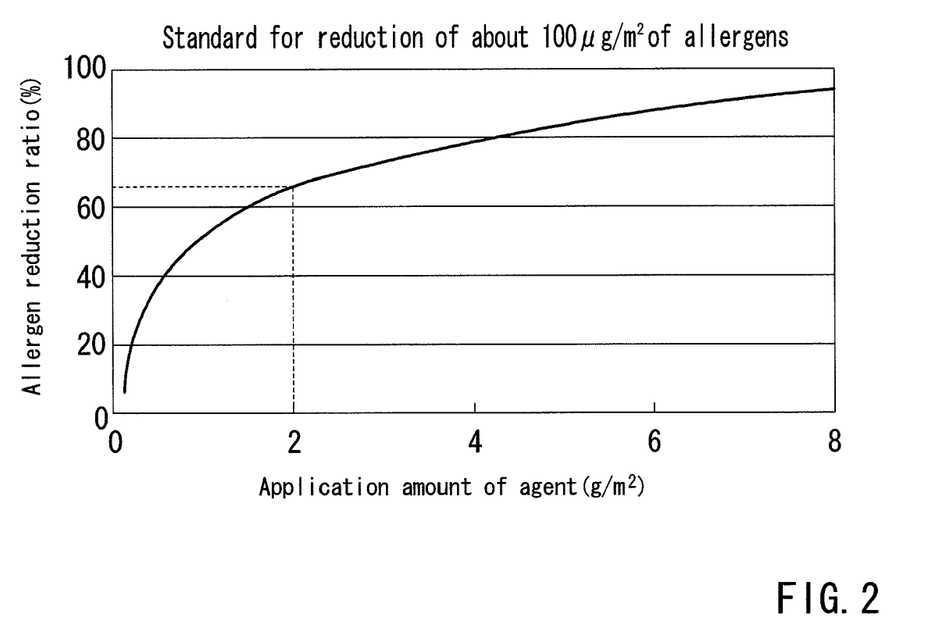
FIG. 2 is a graph showing an allergen reduction ratio when an antiallergenic treatment was performed against 100 μgm$^2$ of allergens.

In FIG. 2, the horizontal axis represents an application amount [g/m²] of an antiallergenic agent and the longitudinal axis represents an allergen reduction ratio [%]. The experimental evidence of the graph shown in FIG. 2 is disclosed in JP-A-2004-290922, the contents of which is incorporate herein by reference. Thus, a detailed description of this graph is omitted here.

As shown in the graph of FIG. 2, by applying an antiallergenic agent to a surface layer in an amount of 2.0 g/m², it is possible to reduce 100 µg/m² of allergens by about 70%. An accumulated amount of allergens on a surface layer of a vehicle seat of a car used for 5 years is about 73 µg/m². Therefore, by applying an antiallergenic agent to a surface layer in an amount of 2.0 µm² or more, it is possible to almost surely reduce or inactivate allergens accumulated on the surface layer.

Accordingly, an amount of the antiallergenic agent adhered to the surface layer is preferably 2.0 g/m² or more, more preferably 3.0 g/m² or more.

As described above, by adhering the antiallergenic agent to a surface layer in an amount of 2.0 g/m² or more (more preferably 3.0 g/m² or more), it is possible to reduce allergens in an amount of 73 µg/m² or more in 5 years.

In the vehicle seat 10, a surface layer covering at least one or more portions of the top plate main portion 12, the top plate side portions 14, the outside portions 16, the seat back portion 18 and the headrest portion 20 has been subjected to the antiallergenic treatment. As described above, there is a tendency that most allergens are accumulated on these portions, therefore, allergens can be more effectively and efficiently reduced.

In addition, there is a tendency that most allergens are accumulated particularly on the top plate main portion, the top plate side portions, and the seat back portion among these portions. Therefore, by subjecting a surface layer covering at least one or more portions of the top plate main portion 12, the top plate side portions 14, and the seat back portion 18 to the antiallergenic treatment, allergens can be further more effectively reduced.

In the vehicle seat, the kind or form of the fabric material (cloth or textile) to be used for the surface layer is not particularly limited. Examples of a fiber for forming the fabric material include natural fibers such as cotton, hemp, wool, and silk, regenerated fibers such as cupra and rayon, semi-synthetic fibers such as acetate, synthetic fibers such as polyester fibers, acrylic fibers, polyamide fibers (such as nylon), and polyolefin fibers, and composite fibers made from any of these fibers, and cotton blend fibers.

The solvent to be used in the antiallergenic agent is not particularly limited as long as it can dissolve or disperse the allergen reducing substance serving as an active ingredient. Examples of the solvent include water, alcohols (such as methyl alcohol, ethyl alcohol, and propyl alcohol), hydrocarbons (such as toluene, xylene, methylnaphthalene, kerosene, and cyclohexane), ethers (such as dimethyl ether, tetrahydrofuran, and dioxane), ketones (such as acetone and methyl ethyl ketone), and amides (such as N,N-dimethylformamide). In particular, alcohols, ethers, and ketones are preferred.

In addition, in the antiallergenic agent, a pharmaceutical aid such as a wetting agent, an antioxidant or an ultraviolet absorber can be blended within a range which does not impair the effectiveness of its allergen reducing activity, and also a miticide, a bactericide, a fungicide, a deodorant or the like can be blended.

In the vehicle seat, examples of the allergens targeted by the antiallergenic agent include animal allergens and plant allergens such as pollens. The allergen reducing agent to be contained in the antiallergenic agent as an active ingredient reduces allergens present in an area to which the agent is applied by suppressing a reaction between these allergens and specific antibodies. As for the animal allergens in which the antiallergenic agent is particularly effective, any types of allergens of mites (Acari, organisms which belong to the order Acari in the class Arachnida in the phylum Arthropoda and are roughly classified into 7 suborders, that is, Notostigmata represented by Opilioacaridae, Tetrasigmata represented by hard tick, Metastigmata represented by Ixodes ovatus and Argas japonicus, Mesostigmata represented by Omithonyssus bacoti and Dermanyssus hirund, Prostigmata represented by Cheyletus malaccensis and Tarsonemus granarius, Astigmata represented by Tyrophagus putrescentiae and Dermatophagoides farinae, and Cryptostigmata represented by Haplochthonius simplex and Cosmochthonius reticulatus) can be targeted. Here, the antiallergenic agent is particularly effective in mites of the genus Dennatophagoides in the family Pyroglyphidae which cause allergic diseases and are abundantly present in the house dust, particularly in bedding.

As described above, with the use of the vehicle seat according to the invention, allergens in the interior of a car can be more effectively reduced or inactivated.

What is claimed is:

1. A vehicle seat comprising;
a surface layer made of a fabric material, wherein
the surface layer covering at least one of a top plate main portion, top plate side portions, outside portions, a seat back portion, and a headrest portion has been subjected to an antiallergenic treatment, and wherein
the antiallergenic treatment is a treatment in which a back side surface of the surface layer is dipped in an antiallergenic agent containing an aromatic hydroxy compound as an active ingredient and an amount of the antiallergenic agent adhered to the surface layer is 2.0 g/m$^2$ or more.

2. A vehicle seat comprising;
a surface layer made of a fabric material, wherein
the surface layer covering at least one of a top plate main portion, top plate side portions, outside portions, a seat back portion and a headrest portion has been subjected to an antiallergenic treatment, and wherein
the antiallergenic treatment results in an amount of an antiallergenic agent being adhered to the surface layer that is 2.0 g/m$^2$ or more and is effective for at least 3 years by reducing 44 μg/m$^2$ or more of allergens.

3. The vehicle seat according to claim 2, wherein the antiallergenic treatment is a treatment in which a back side surface of the surface layer is dipped in the antiallergenic agent.

4. A vehicle seat comprising;
a surface layer made of a fabric material, wherein
the surface layer covering at least one of a top plate main portion, top plate side portions, outside portions, a seat back portion and a headrest portion has been subjected to an antiallergenic treatment, and wherein
the antiallergenic treatment results in an amount of an antiallergenic agent being adhered to the surface layer that is 2.0 g/m$^2$ or more and is effective for at least 5 years by reducing 73 μg/m$^2$ or more of allergens.

5. The vehicle seat according to claim 4, wherein the antiallergenic treatment is a treatment in which a back side surface of the surface layer is dipped in the antiallergenic agent.

* * * * *